United States Patent [19]

Weisse et al.

[11] Patent Number: 5,364,983
[45] Date of Patent: Nov. 15, 1994

[54] PROCESS FOR THE PREPARATION OF AROMATIC POLYHYDROXY COMPOUNDS

[75] Inventors: Laurent Weisse, Oberursel; Heinz Strutz, Usingen, both of Germany

[73] Assignee: Hoechst Aktiengesellschaft, Frankfurt, Germany

[21] Appl. No.: 133,660

[22] Filed: Oct. 7, 1993

[30] Foreign Application Priority Data

Oct. 9, 1992 [DE] Germany ............................ 4233989

[51] Int. Cl.⁵ .............................................. C07C 37/00
[52] U.S. Cl. .................................... 568/771; 568/741; 568/763; 568/768; 568/803
[58] Field of Search ............... 568/741, 768, 771, 763, 568/803, 800

[56] References Cited

U.S. PATENT DOCUMENTS

| | | | |
|---|---|---|---|
| 3,585,243 | 6/1971 | Gradeff | 568/771 |
| 4,209,648 | 6/1980 | Cottman | 568/766 |
| 4,435,601 | 3/1984 | Formaneck et al. | 568/430 |
| 4,533,766 | 8/1985 | Drauz et al. | 568/771 |
| 5,120,884 | 6/1992 | Thomas et al. | 568/734 |

FOREIGN PATENT DOCUMENTS

| | | |
|---|---|---|
| 2031483 | 6/1991 | Canada . |
| 69070 | 2/1986 | European Pat. Off. . |
| 436410 | 7/1991 | European Pat. Off. . |
| 2447971 | 5/1975 | Germany . |
| 3308769 | 1/1985 | Germany . |
| 2059234 | 3/1987 | Japan .................................. 568/771 |

OTHER PUBLICATIONS

Muller, E., Houben-Weyl, "Methoden Der Organischen Chemie": vol. VI/lc, Stuttgart, Georg Thieme Verlag, 1976, pp. 286–308.

March, J., Advanced Organic Chemistry, N.Y., John Wiley & Sons, 1983, p. 496.

Nikaido, M., et al, J. Org. Chem. 49:4740–4741 (1984).

Syper, L., Synthesis: 167–172 (Mar., 1989).

K. F. Wedemeyer "Methoden Der Organischen Chemie" (Houben-Weyl) Band VI/1C, 1976, pp. 286–308.

Primary Examiner—Werren B. Lone
Attorney, Agent, or Firm—Connolly & Hutz

[57] ABSTRACT

The present invention relates to a process for the preparation of aromatic polyhydroxy compounds, by reacting an aromatic hydroxyaldehyde with hydrogen peroxide, with or without the addition of a base, in the presence of a nitrile R—CN, in which R is an alkyl radical having 1 to 4 carbon atoms or a phenyl radical, which is unsubstituted or substituted by one or more alkyl groups.

17 Claims, No Drawings

PROCESS FOR THE PREPARATION OF AROMATIC POLYHYDROXY COMPOUNDS

DESCRIPTION

The present invention relates to a process for the preparation of aromatic polyhydroxy compounds by oxidation of the corresponding aromatic hydroxyaldehydes.

Aromatic polyhydroxy compounds, in particular aromatic dihydroxy compounds, are of great industrial importance in the preparation of dyes, in the production of plastics, in the preparation of important crop protection agents or in photography (DE-A 24 47 971; EP 69 070; DE-C 3 308 769).

To produce this industrially relevant compound class, a multiplicity of methods is known, most of which, however, proceed unselectively (Advanced Organic Chemistry, 1983, McGraw-Hill, Tokyo, 496).

In EP 436 410, a selective synthesis of substituted hydroquinones is described. According to this, o-cresol is initially regioselectively acetylated in the para position and the product is then converted by the Dakin oxidation into methyl hydroquinone. The disadvantage of the process is, in addition to the use of expensive acetyl chloride, the stoichiometric consumption, based on the starting material, of a base.

The Dakin oxidation of hydroxybenzaldehydes also requires, according to the teaching of U.S. Pat. No. 3,585,243, an addition of at least half an equivalent of base per mole of hydroxybenzaldehyde.

The Baeyer-Villiger oxidation of hydroxybenzaldehydes (Houben-Weyl, Methoden der Organischen Chemie, [Methods in Organic Chemistry], volume VI 1c, 1976; Synthesis (1989) 167) has the advantage, compared with the Dakin oxidation, of generally only forming volatile acids as coupling products. However, the corresponding peracids, such as performic acid or peracetic acid, are not hazard-free from the safety aspect and often lead to the acid esters of the corresponding polyhydroxy aromatic compounds, which then have to be laboriously separated as by-products or main products or hydrolyzed in an additional step.

A variant of this method is the acid-catalyzed Baeyer-Villiger oxidation using hydrogen peroxide as oxidant and methanol as solvent. However, in this process, per mole of starting material 15 to 75 molar % of an acid are required, which must be neutralized after completion of the reaction (J. Org. Chem. 49 (1984) 4740). In addition, in this process only protected phenols, that is in the form of their methyl ethers, are used as starting substances.

There is therefore a requirement for a process which avoids the disadvantages of the above-described procedures. The process should, moreover, be able to be carried out simply and to use industrially readily available auxiliaries. Moreover, it should deliver the desired product of value without great technical effort in high yield and high purity.

This object is achieved by a process for the preparation of aromatic polyhydroxy compounds. It comprises reacting an aromatic hydroxyaldehyde with hydrogen peroxide, with or without the addition of a base, in the presence of a nitrile R-CN, in which R is an alkyl radical having 1 to 4 carbon atoms or a phenyl radical, which is unsubstituted or substituted by one or more alkyl groups.

The starting material generally used is an aromatic hydroxyaldehyde of the formula (I)

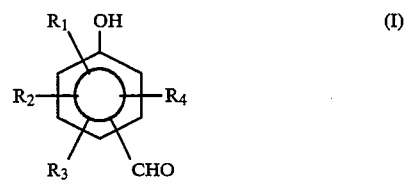

in which $R_1$, $R_2$, $R_3$ and $R_4$ are identical or different and are hydrogen, an alkyl radical having 1 to 20 carbon atoms, an aryl radical having 6 to 14 carbon atoms, an alkoxy radical having 1 to 10 carbon atoms, an arylalkyl radical having 7 to 20 carbon atoms, an alkylaryl radical having 7 to 20 carbon atoms, an aryloxy radical having 6 to 10 carbon atoms, a fluoroalkyl radical having 1 to 10 carbon atoms, a haloaryl radical having 6 to 10 carbon atoms, a halogen atom or a hydroxyl radical or $R_1$, $R_2$, $R_3$ and/or $R_4$, together with the respective connecting carbon atoms of the aromatic nucleus, form one or more substituted or unsubstituted rings.

It is expedient to use an aromatic hydroxyaldehyde of the formula (I), in which $R_1$, $R_2$, $R_3$ and $R_4$ are identical or different and are hydrogen, an alkyl radical having 1 to 10 carbon atoms, an alkoxy radical having 1 to 4 carbon atoms, an aryloxy radical having 6 to 10 carbon atoms, a fluoroalkyl radical having 1 to 6 carbon atoms, a halogen atom or a hydroxyl radical or $R_1$ and $R_2$, $R_2$ and $R_3$ and/or $R_3$ and $R_4$, together with the respective connecting carbon atoms of the aromatic nucleus, form a substituted or unsubstituted, saturated or unsaturated ring having 5 or 6 atoms.

In the process according to the invention, an aromatic hydroxyaldehyde of the formula (I) can be used highly successfully, in which $R_1$, $R_2$, $R_3$ and $R_4$ are identical or different and are an alkyl radical having 1 to 4 carbon atoms, an alkoxy radical having 1 to 4 carbon atoms, a halogen, in particular fluorine or chlorine, or a hydroxyl radical, or $R_1$ and $R_2$, $R_2$ and $R_3$ or $R_3$ and $R_4$, together with the respective connecting carbon atoms of the aromatic nucleus, form an unsaturated ring having 6 carbon atoms.

Particularly suitable starting materials are aromatic hydroxyaldehydes of the formula (I) which have a single hydroxyl radical and the hydroxyl radical and the aldehyde group are situated in the 1,2- or 1,4-position relative to each other. Representatives of this group by name are 2-hydroxybenzaldehyde and 4-hydroxybenzaldehyde.

Generally, only one aromatic hydroxyaldehyde is used in the reaction. However, it is also possible to use mixtures of two or more aromatic hydroxyaldehydes as starting material.

To carry out the process, the aromatic hydroxyaldehyde, the nitrile R—CN and hydrogen peroxide are combined, with or without the addition of a base and/or a solvent, and reacted with mixing. If necessary, the use of the base can be omitted, but addition of the base leads to an acceleration of the reaction. If desired, a solvent, for example an aliphatic alcohol having 1 to 4 carbon atoms, methylacetate, ethylacetate or mixtures thereof can be used. However, if necessary, the solvent can also be dispensed with without having to accept disadvantages. When the individual substances are added, there is no restriction to a particular sequence. The individual substances can be metered in simultaneously or they can be added sequentially and the process can proceed continuously or discontinuously.

It is particularly simple to take the aromatic hydroxyaldehyde and the nitrile or a mixture of both substances and then to meter in the hydrogen peroxide or a mixture of hydrogen peroxide and nitrile.

The molar ratio of aromatic hydroxyaldehyde:nitrile can be chosen within broad limits. It is expediently 1:(1 to 50), in particular 1:(5 to 40), preferably 1:(10 to 30). Nitrile used in excess serves as solvent, if required.

The aromatic hydroxyaldehyde is reacted in the presence of a nitrile R—CN, in which R is an alkyl radical having 1 to 4, in particular 1 to 2, carbon atoms or a phenyl radical, which is unsubstituted or substituted by one or more alkyl groups, in particular alkyl groups having 1 to 4 carbon atoms, in particular an unsubstituted phenyl radical. Mixtures of two or more of the abovementioned nitriles may also be used. Highly suitable nitriles are acetonitrile and benzonitrile, in particular acetonitrile.

The amount of hydrogen peroxide required for the reaction depends on the aldehyde equivalents which are to be oxidized. Conventionally, per equivalent of aromatic hydroxyaldehyde or per mole of aromatic hydroxyaldehyde, 0.5 to 5, in particular 0.8 to 2, preferably 0.9 to 1.5 mol of hydrogen peroxide are used. In most cases, aromatic hydroxyaldehyde and hydrogen peroxide are used in the ratio 1:(1 to 1.2).

Hydrogen peroxide is used in the form of its aqueous solutions having a content of 3 to 90, in particular 5 to 60, preferably 10 to 30% by weight of $H_2O_2$. In place of hydrogen peroxide, hydrogen-peroxide-forming substances or mixtures can alternatively be used. The use of aqueous hydrogen peroxide permits particularly simple working.

As previously mentioned, it is expedient, to accelerate the reaction, to use a base in a subsidiary amount. Conventionally, per equivalent of aromatic hydroxyaldehyde or per mole of aromatic hydroxyaldehyde, 0.001 to 0.05 mol of base is added. Bases which are useful are alkali metal hydroxides and alkaline earth metal hydroxides and/or alkali metal carbonates, in particular sodium hydroxide, potassium hydroxide and/or sodium carbonate.

The reaction is carried out at −30° to 100° C., in particular −10° to 80° C., preferably 20° to 70° C., where thorough mixing of the reactants is to be ensured.

After completion of the reaction, any hydrogen peroxide still present or residual peroxide, which can have formed during the reaction, is destroyed by known1 methods, for example by addition inter alia of activated charcoal, Pd on activated charcoal, or sodiumsulfite, and the nitrile is substantially distilled off, if required under reduced pressure. The residue is then taken up in a suitable solvent, for example ethyl acetate, water or a saturated aqueous salt solution, in particular a saturated aqueous NaCl solution is added, the organic phase is separated off and the aqueous phase is extracted repeatedly with the same solvent. The amide situated in the aqueous phase, in particular acetamide, can be isolated as a product of value or returned to nitrile by known processes (Beyer, Lehrbuch der organischen Chemie, [Textbook of Organic Chemistry], Hirzel Verlag Stuttgart, 1981, p. 252). The organic phases are combined, dried and freed from solvent by distillation. The residue produced in this already contains the valuable product in high purity (≧95%).

The process can be carried out particularly easily under atmospheric pressure. If desired, it is also possible to work beneath or above atmospheric pressure.

The process according to the invention is distinguished not only by an almost quantitative conversion of the aromatic hydroxyaldehyde, but also by an unusually high selectivity with respect to the formation of the desired polyhydroxy compounds. By-products, such as hydroxycarboxylic acids and hydroxycarboxylic esters are not formed. Therefore, a complex purification of the reaction product produced can generally be dispensed with.

Since the base is only added on a small scale (catalytic quantities), environmentally polluting salts and salt-laden waste waters are likewise produced only in very low amounts. Accordingly, the process according to the invention proves to be environmentally friendlier compared to the processes of the prior art, which produce a considerably larger amount of salts.

The following examples verify the invention without restricting it.

EXPERIMENTAL SECTION

EXAMPLE 1

Preparation of catechol (o-dihydroxybenzene)

6.1 g (0.05 mol) of salicylaldehyde and 0.01 g (0.25 mmol) of NaOH in 50 ml (0.96 mol) of acetonitrile are taken and 17.2 g of an 11.8% strength (0.06 mol) aqueous hydrogen peroxide solution are added and the mixture is stirred for 48 hours at 50° C.

Any peroxides still present are removed by a dilute sodium sulfite solution- Ethyl acetate is then added to the reaction mixture, the organic phase is separated off and the aqueous phase is washed repeatedly with ethyl acetate. The combined and dried organic phases are then freed from solvent in vacuo, 5.4 g of a solid being obtained, which is identified as catechol by $^1$H-NMR spectroscopy with reference to a comparison sample.

(Purity determined by gas chromatography: 98%; yield 96% of theory).

EXAMPLE 2

Preparation of hydroquinone (p-dihydroxybenzene)

6.1 g (0.05 mol) of p-hydroxybenzaldehyde and 0.05 g (1.25 mmol) of NaOH are reacted for 24 hours and worked up analogously to Example 1. 5.35 g of a solid are obtained, which is identified as hydroquinone by $^1$H-NMR spectroscopy with reference to a comparison sample.

(Purity determined by gas chromatography: 98%; yield: 95% of theory).

EXAMPLE 3

Preparation of 2,3-Dimethylhydroquinone 15 g (0.1 mol) of 3,5-dimethyl-4-hydroxybenzaldehyde, 0.1 g (2.5 mmol) of NaOH and 34.4 g of an 11.8% strength (0.12 mol) aqueous hydrogen peroxide solution are reacted and worked up analogously to Example 1. 13.7 g of a solid are obtained, which is identified as 2,3-dimethylhydroquinone by $^1$H-NMR spectroscopy with reference to a comparison sample.

(Purity determined by gas chromatography: 98%; yield 97% of theory).

EXAMPLE 4

Preparation of catechol 6.1 g (0.05 mol) of salicylaldehyde and 33 g of a 12.6% strength (0.13 mol) aqueous hydrogen peroxide solution are reacted for 70 hours at 50° C. and worked up analogously to Example 1, but without addition of base. 5.4 g of a solid are obtained, which is identified as catechol by $^1$H-NMR spectroscopy with reference to a comparison sample.

(Purity determined by gas chromatography: 90%; yield 88% of theory).

We claim:

1. A process for the preparation of aromatic polyhydroxy compounds, which comprises reacting an aromatic hydroxyaldehyde with hydrogen peroxide, with or without the addition of a base, in the presence of a nitrile R—CN, in which R is an alkyl radical having 1 to 4 carbon atoms or a phenyl radical, which is unsubstituted or substituted by one or more alkyl groups.

2. The process as claimed in claim 1, wherein an aromatic hydroxyaldehyde is used of the formula (I)

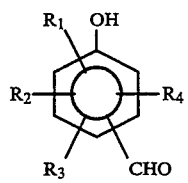

in which $R_1$, $R_2$, $R_3$ and $R_4$ are identical or different and are hydrogen, an alkyl radical having 1 to 20 carbon atoms, an aryl radical having 6 to 14 carbon atoms, an alkoxy radical having 1 to 10 carbon atoms, an arylalkyl radical having 7 to 20 carbon atoms, an alkylaryl radical having 7 to 20 carbon atoms, an aryloxy radical having 6 to 10 carbon atoms, a fluoroalkyl radical having 1 to 10 carbon atoms, a haloaryl radical having 6 to 10 carbon atoms, a halogen atom or a hydroxyl radical or $R_1$, $R_2$, $R_3$ or $R_4$, or mixtures thereof, together with the respective connecting carbon atoms of the aromatic nucleus, form one or more substituted or unsubstituted rings.

3. The process as claimed in claim 1, wherein an aromatic hydroxyaldehyde of the formula (I) is used, in which $R_1$, $R_2$, $R_3$ and $R_4$ are identical or different and are hydrogen, an alkyl radical having 1 to 10 carbon atoms, an alkoxy radical having 1 to 4 carbon atoms, an aryloxy radical having 6 to 10 carbon atoms, a fluoroalkyl radical having 1 to 6 carbon atoms, a halogen atom or a hydroxyl radical or $R_1$ and $R_2$, $R_2$ and $R_3$ or $R_3$ and $R_4$, together with the respective connecting carbon atoms of the aromatic nucleus, form a substituted or unsubstituted, saturated or unsaturated ring having 5 or 6 atoms.

4. The process as claimed in claim 1, wherein an aromatic hydroxyaldehyde of the formula (I) is used, in which $R_1$, $R_2$, $R_3$ and $R_4$ are identical or different and are an alkyl radical having 1 to 4 carbon atoms, an alkoxy radical having 1 to 4 carbon atoms, a halogen, in particular fluorine or chlorine, or a hydroxyl radical, or $R_1$ and $R_2$, $R_2$ and $R_3$ or $R_3$ and $R_4$, together with the respective connecting carbon atoms of the aromatic nucleus, form an unsaturated ring having 6 carbon atoms.

5. The process as claimed in claim 1 wherein the aromatic hydroxyaldehyde of the formula (I) has a single hydroxyl radical and the hydroxyl radical and the aldehyde group are situated in the 1,2- or 1,4-position relative to each other.

6. The process as claimed in claim 1, wherein, per mole of aromatic hydroxyaldehyde, 1 to 50 moles of the nitrile are present.

7. The process as claimed in claim 1, wherein the nitrile is acetonitrile or benzonitrile or a mixture thereof.

8. The process as claimed in claim 1, wherein, per mole of aromatic hydroxyaldehyde, 0.5 to 5 moles of hydrogen peroxide are reacted with the aromatic hydroxyaldehyde.

9. The process as claimed in claim 1, wherein, per mole of aromatic hydroxyaldehyde, 0.001 to 0.05 mol of base are used.

10. The process as claimed in claim 1, wherein the base used is an alkali metal hydroxide, an alkaline earth metal hydroxide or an alkali metal carbonate or mixture thereof.

11. The process as claimed in claim 1, wherein the reaction is carried out at −30° to 100° C.

12. The process as claimed in claim 1, wherein, per mole of aromatic hydroxyaldehyde, 5 to 40 moles of the nitrile are present.

13. The process as claimed in claim 12, wherein 10 to 30 moles of the nitrile are present.

14. The process as claimed in claim 1, wherein the nitrile is acetonitrile.

15. The process as claimed in claim 1, wherein the amount of hydrogen peroxide reacted with the aromatic hydroxyaldehyde is 0.8 to 2 moles, per mole of aromatic hydroxyaldehyde.

16. The process as claimed in claim 15, wherein said amount is 0.9 to 1.5 mole.

17. The process as claimed in claim 1, wherein the reaction is carried out at −10° to 80° C.

* * * * *